US00PP10442P

United States Patent [19]

Egger

[11] Patent Number: Plant 10,442

[45] Date of Patent: Jun. 9, 1998

[54] ASIATIC HYBRID LILY PLANT NAMED 'CEB PAINT'

[75] Inventor: Donald L. Egger, Wilsonville, Oreg.

[73] Assignee: Cebeco Lilies, Inc., Aurora, Oreg.

[21] Appl. No.: 788,117

[22] Filed: Jan. 23, 1997

[51] Int. Cl.[6] ..... A01H 5/00

[52] U.S. Cl. ..... Plt./87.4

[58] Field of Search ..... Plt./87.4

[56] References Cited

U.S. PATENT DOCUMENTS

P.P. 6,206 6/1988 McRae ..... Plt./87.4

P.P. 7,630 8/1991 Veenstra ..... Plt./87.4

*Primary Examiner*—James R. Feyrer

*Assistant Examiner*—Kent L. Bell

*Attorney, Agent, or Firm*—Klarquist Sparkman Campbell Leigh & Whinston

[57] ABSTRACT

A new and distinct upright Asiatic Lily Hybrid having deep yellow flowers with unique, contrasting deep red blotches above the nectary of each tepal, and large yellow buds on genetically dwarf stems with dense foliage excellent for pot plant production.

1 Drawing Sheet

BACKGROUND OF THE INVENTION

The present invention relates to a new and distinct cultivar of Lily hybrid referred to commercially as an upright Asiatic hybrid pot lily and given the cultivar name 'Ceb Paint'.

This invention was developed by controlled breeding in Aurora, Oreg. using A-107-80, a propietary, non-released plant as the seed parent, and A-069-80, another propietary, non-released plant as the pollen parent.

This invention has not been observed under all possible environmental conditions. The phenotype may vary signfiicantly with variations in environment such as temperature, light intensity and day length, without, however, any variation in genotype.

The following traits have been repeatedly observed and are determined to be the basic characteristics of this invention which in combination distinguish this lily as a new and distinct cultivar: 1) large flowers of a deep yellow with a contrasting dark red blotch at the base of each tepal and matching dark red anthers and stigma; 2) beautiful, large, bright yellow buds; 3) genetically dwarf stems excellent for pot plant production; 4) very good bud count; 5) good vigor; 6) good, dense foliage. Bulbs of this plant may be precooled and forced out of season for uniform pot plant production. In addition, this new lily shows good disease resistance.

This invetion is best compared to 'Butter Pixie' (U.S. Plant Pat. No. 6,422) This invention is similar to 'Butter Pixie' except for its unique, contrasting dark red blotch and matching dark red anthers and stigma.

Asexual reproduction of this new variety has been accomplished at Cebeco Lilies, Inc., Aurora, Oreg. by scaling and tissue culture. The resulting plants have shown that the above-mentioned unique features are stable and reproduce true to type in each successive propagation.

Figure 2:
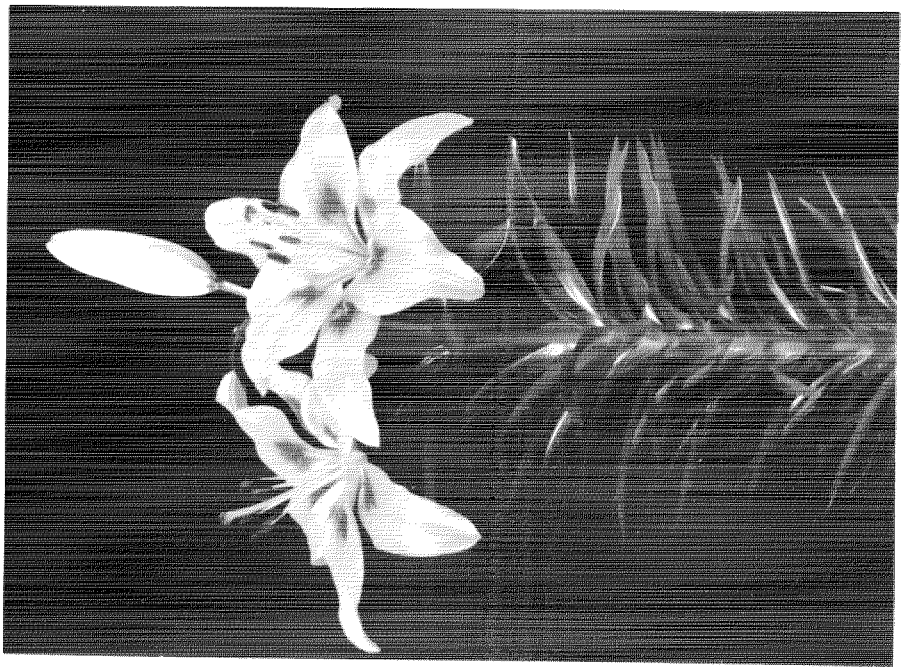
FIG. 2 is a photograph showing the 'Ceb Paint' lily.
Figure 1:
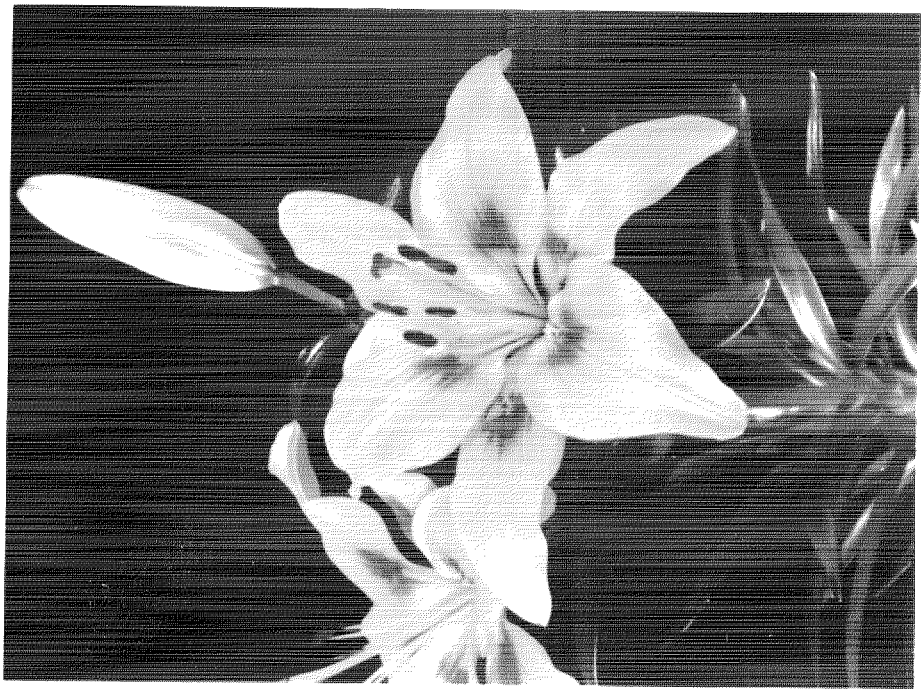
FIG. 1 is a close-up photograph which illustrates in greater detail a single flower of the new plant.

The photographs of the drawing were taken in July 1995 in a studio and illustrate the typical flower and foliage form, with color as true as reasonably possible in this type of color photograph.

DETAILED DESCRIPTION

The following is a detailed description of the invention based on plants produced under commercial practices in the Cebeco Lilies, Inc. greenhouse in Aurora, Oreg. in July 1995. Color references are made to The Royal Horticultural Society Colour Chart, except where the context indicates a term having its ordinary dictionary meaning.

The Plant

Origin: Seedling.

Parentage:

*Seed parent.*—A-107-80.

*Pollen parent.*—A-069-80.

Commercial Classification: Hybrid Asiatic Lily, pot type.

Classification: Division I-A, Upright Asiatic Hybrid Lily, according to The Horticultural Classification of Lilies by The Royal Horticultural Society of London.

Form: Single erect stem bearing terminal cluster of flowers.

Height: About 51 cm. from the top of the soil to the top of the flowers from bulbs of 12–14 cm. in circumference.

Stem color: Yellow green (144A).

Growth habit: Vigorous upright and rigid.

Internode length: About 2 to 7 mm.

Foliage:

*Arrangement.*—Spiral.

*Leaf size.*—To about 50–95 mm. long and 9–11 mm wide.

*Leaf shape.*—Lanceolate.

*Texture.*—Leathery.

*Aspect.*—Glossy.

*Color.*—Medium green on both sides. Closest to Yellow green group 147A with the bottomside slightly lighter.

Bulbs:

*Size.*—Variable, raging to about 12–14 cm. in circumference as used commercially.

*Color.*—White.

The Bud.

Size; Large, to about 80 mm. long and 25 mm. wide just prior to opening.

Shape: Ovoid with an obtuse tip.

Rate Of Opening: The mature bud opens slowly in response to light.

Color: Yellow. Yellow group 12B.

The Flower

Blooming habit: Annually, once and early season.

Days to bloom: Flowers approximately 69 days after spring greenhouse planting under typical commercial flower forcing conditions of 15 degrees Celsius night time temperatures.

*Flower size: Medium-large.*

*Diameter.*—About 13 cm.

*Depth.*—About 5.5 cm.

Borne: In an umbel-like raceme if 2–4 flowers are present and with branched pedicels if 5 or more flowers are present.

Shape: When the flower first opens it is a bowl shape. Later the shape flattens out more and the tepals reflex slightly at the tips.

Tepalage:

*Number.*—Six.

*Arrangement.*—Imbricated.

*Shape.*—Ovate.

*Texture.*—Spongy, waxy, and thick.

*Aspect.*—Satiny.

*Size.*—Length: About 9 cm. Width: Inner tepals — about 46 mm. Outer Tepals — about 30 mm. Depth of imbrication: About 9 cm.

*Nectary.*—Yellow green with white glandular pubescence on the bottom ⅔ and yelllow with white glandular pubescence on the top ⅓; channels together.

*Projections.*—Present as raised lines alongside nectary and some terminating with spots.

*Spots.*—Very few, 0–8. Greyed-purple group 187A.

*Blush.*—Dark red. Above the nectary, made up of many, very small dots of color, Red 46A. Grown cooler the blotch will be larger, spreading to the margins.

*Color.*—Topside: Vibrant yellow. Closest to Yellow Group 12A, but more intense. Blotch color is dark red, Red 46. Bottomside: Yellow 12A on the edge to lighter toward midrib.

*Discoloration.*—Very little, darkens slightly with age.

*Fragrance.*—None.

Peduncle:

*Length.*—About 5–9 cm.

*Color.* —Yellow green (144A).

*Orientation.*—Ascending upwardly in a curve to about 45° from the horizontal.

The Reproductive Organs

Stamens:

*Number.*—Six, typical of the genus Lilium.

*Anthers before dehiscence.*—Size: About 18 mm. Color: Red Brown. Greyed-orange group 166A.

*Filaments.*—Length: About 60 mm. Color: Yellow Yellow group 12A.

*Pollen.*—Color: Greyed orange 172A.

Pistil.

*Number.*—One.

*Style.*—Length: About 57 mm.

*Color: Yellow. Yellow group* 12A.

*Stigma.*—Color: Red 46A in the form of many small red dots on a yellow stigma.

The Fruit

Fertility: Fertile.

Shape: Ovoid.

Color of maturity: Soft brown.ps

I claim:

1. A new and distinct cultivar of Asiatiic hybrid lily plant substantially as herein shown and described.

* * * * *

UNITED STATES PATENT AND TRADEMARK OFFICE

CERTIFICATE OF CORRECTION

PATENT NO. : PP 10,442
DATED : June 9, 1998
INVENTOR(S) : Donald L. Egger

It is certified that error appears in the above-identified patent and that said Letters Patent is hereby corrected as shown below:

Column 2,
Line 29, change "Vigorous upright" to -- Vigorous, upright --

Column 3,
Line 2, change "Size;" to -- Size: --
Line 33, change "9 cm." to -- 9 mm. --

Column 4,
Line 7, change "Red 46." to -- Red 46A. --
Line 11, change "Peduncle:" to -- Pedicle --
Line 23, change "Yellow Yellow" to -- Yellow. Yellow --
Line 26, change "Pisti." to -- Pistil: --
Line 37, change "Color of maturity: Soft brown.ps" to -- Color at maturity: Soft Brown. --

Signed and Sealed this

Twenty-third Day of April, 2002

*Attest:*

*Attesting Officer*

JAMES E. ROGAN
*Director of the United States Patent and Trademark Office*